United States Patent [19]

Kawaguchi et al.

[11] Patent Number: 5,735,839
[45] Date of Patent: Apr. 7, 1998

[54] SHORTS TYPE DISPOSABLE DIAPER

[75] Inventors: Haruko Kawaguchi; Masao Kurahashi; Harumitsu Toyoda, all of Haga-gun, Japan

[73] Assignee: Kao Corporation, Tokyo, Japan

[21] Appl. No.: 652,566

[22] PCT Filed: Oct. 11, 1995

[86] PCT No.: PCT/JP95/02077

§ 371 Date: Jun. 11, 1996

§ 102(e) Date: Jun. 11, 1996

[87] PCT Pub. No.: WO96/11657

PCT Pub. Date: Apr. 25, 1996

[30] Foreign Application Priority Data

Oct. 14, 1994 [JP] Japan ................. 6-249760
Oct. 14, 1994 [JP] Japan ................. 6-249761

[51] Int. Cl.$^6$ ......................................... A61F 13/15
[52] U.S. Cl. .......................................... 604/385.2
[58] Field of Search ...................... 604/385.1, 385.2, 604/358, 379, 380, 386, 389, 392, 394, 396

[56] References Cited

U.S. PATENT DOCUMENTS 5,163,932  11/1992  Nomura et al. .............. 604/385.2
5,340,424  8/1994   Matsushita ................... 604/385.2
5,415,649  5/1995   Watanabe et al. .
5,449,353  9/1995   Watanabe et al. .
5,569,232  10/1996  Roe et al. .................... 604/385.2

FOREIGN PATENT DOCUMENTS 4-161152   6/1992   Japan ......................... 604/385.2
4-166150   6/1992   Japan .
4-371148   12/1992  Japan .
2253131    9/1992   United Kingdom ........ 604/385.2
94/09736   5/1994   WIPO .......................... 604/385.2

Primary Examiner—John G. Weiss
Assistant Examiner—Ki Tong O
Attorney, Agent, or Firm—Birch, Stewart, Kolasch & Birch, LLP

[57] ABSTRACT

The shorts type disposable diaper (1) of the present invention is characterized by a plurality of elastic members (4) provided at the urination point (40) located below the body-surrounding portion (30) and in the vicinity of the urination portion of the wearer, thereby forming continuous gathers in the width direction of the diaper. The shorts type disposable diaper (1) is also characterized by a plurality of elastic members (31) provided at the body-surrounding portion (30) in such a manner that the interval of the elastic members (31) becomes narrower towards the waist opening portion (10) and that the elongation of the elastic members (31) increases towards the waist opening portion (10).

8 Claims, 1 Drawing Sheet

SHORTS TYPE DISPOSABLE DIAPER

TECHNICAL FIELD

This invention relates to a shorts type disposable diaper suitable for use as a diaper for infants and adults, underwear for those suffering from incontinence of urine, or training pants. More particularly, it relates to a shorts type disposable diaper which fits the wearer's body and surely prevents leakage while it is worn.

BACKGROUND ART

Various types of shorts type disposable diapers having a waist opening portion and a pair of leg opening portions have been proposed. As an example of recent proposals, Japanese Patent Application Laid-Open 4-166150 discloses a shorts type disposable diaper in which a plurality of elastic members are provided at a body-surrounding portion which is located between the waist opening portion and the pair of leg opening portions and at which an absorbent member is provided, forming substantially continuous gathers along the entire circumference of the body-surrounding portion. The shorts type disposable diaper disclosed fits the wearer's body very well owing to the elastic members of the body-surrounding portion and surely prevents leakage of discharged waste materials while it is worn.

However, demands for shorts type disposable diapers having further improved leakproofness have recently been increasing. That is, after a wearer discharges the waste materials, even the above-mentioned shorts type disposable diaper gets out of the right position due to the weight of the discharged waste materials, partly swells out into poor appearance, and loses a good fit, tending to hinder the wearer's movement and to cause leakage of the discharged waste materials. Therefore, it has been demanded to develop a shorts type disposable diaper which does not slide down and causes no leakage even after a wearer discharges solid waste materials.

The extensibility (elongation) of the elastic members provided at the body-surrounding portion may be increased so as to prevent sliding of a disposable diaper. However, increased elongation imposes excessive pressure on the wearer's body and considerably reduces comfort. Japanese Patent Application Laid-Open 4-371148 proposes a shorts type disposable diaper having a plurality of elastic members arranged in the body-surrounding portion in such a manner that the interval of the elastic members becomes narrower towards waist opening portion, but the diaper of this type still fails to completely satisfy the above requirement.

DISCLOSURE OF THE INVENTION

It is therefore an object of the present invention to provide a shorts type disposable diaper which, even after waste materials are discharged, does not slide down to cause leakage due to the weight of the waste materials, maintains good fit and appearance without swelling in part.

As a result of extensive investigations, the inventors of the present invention have found that the above object of the present invention can be accomplished by a shorts type disposable diaper having gathers formed at the site which is located in the vicinities of the urination portion for a wearer (the first finding) and a shorts type disposable diaper having elastic members at the body-surrounding portion disposed in such a manner that the interval of the elastic members becomes narrower towards the waist opening portion and that the elongation of the elastic members increases towards the waist opening portion (the second finding).

The present invention has been completed based on the first finding and provides a shorts type disposable diaper comprising an absorbent body which comprises a liquid permeable topsheet, a liquid impermeable backsheet, and an absorbent member interposed between the topsheet and the backsheet, the absorbent body having a front waist body portion located on the stomach side of a diaper wearer when the diaper is worn and a rear waist body portion located on the back side of the wearer, the front and rear waist body portions being joined and sealed together at opposing lateral side edges thereof to form a waist opening portion and a pair of leg opening portions, each of the waist opening portion and the pair of leg opening portions being provided with an elastic member which forms substantially continuous gathers along the entire circumference of the waist opening portion and the leg opening portions, and a plurality of elastic members being provided at a body-surrounding portion which is located between the waist opening portion and the pair of leg opening portions and at which the absorbent member is provided, forming substantially continuous gathers along the entire circumference of the body-surrounding portion, the diaper being characterized in that a plurality of elastic members are provided at a urination point located below the body-surrounding portion and in the vicinity of the urination portion of the wearer, thereby forming continuous gathers in the width direction of the diaper (hereinafter referred to as a first invention).

The present invention has also been completed based on the second finding and provides a shorts type disposable diaper comprising an absorbent body which comprises a liquid permeable topsheet, a liquid impermeable backsheet, and an absorbent member interposed between the topsheet and the backsheet, the absorbent body having a front waist body portion located on the stomach side of a diaper wearer when the diaper is worn and a rear waist body portion located on the back side of the wearer, the front and rear waist body portions being joined and sealed together at opposing lateral side edges thereof to form a waist opening portion and a pair of leg opening portions, each of the waist opening portion and the pair of leg opening portions being provided with an elastic member which forms substantially continuous gathers along the entire circumference of the waist opening portion and the leg opening portions, and a plurality of elastic members being provided at a body-surrounding portion which is located between the waist opening portion and the pair of leg opening portions and at which the absorbent member is provided, forming substantially continuous gathers along the entire circumference of the body-surrounding portion, the diaper being characterized in that the elastic members provided at the body-surrounding portion are disposed in such a manner that the interval of the elastic members becomes narrower towards the waist opening portion and that the elastic members provided at the body-surrounding portion have an increasing elongation towards the waist opening portion (hereinafter referred to as a second invention).

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

An embodiment of the shorts type disposable diaper according to the present invention (inclusive of the first and second inventions) will be described in detail by referring to FIGS. 1 and 2.

Figure 1:
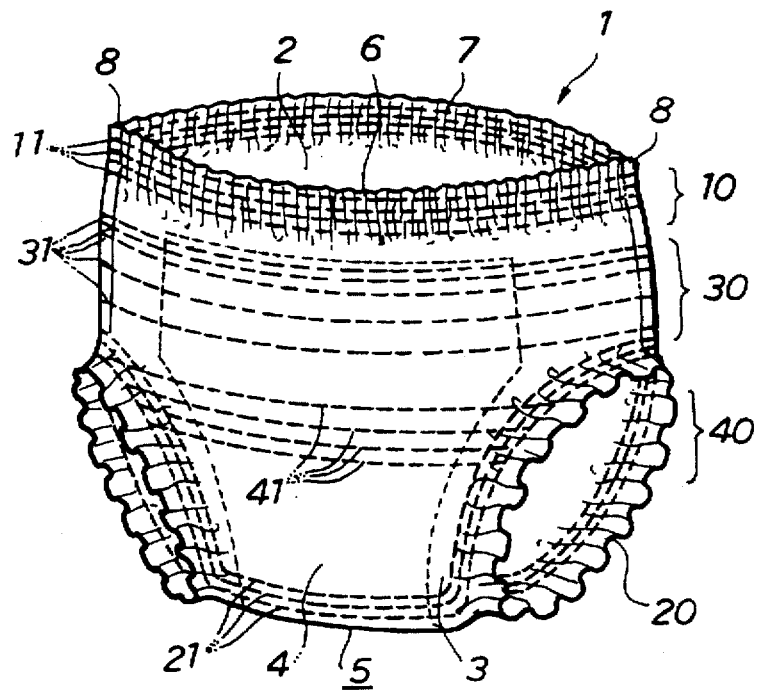
FIG. 1 is a perspective view of a preferred embodiment of the shorts type disposable diaper according to the present invention.
Figure 2:
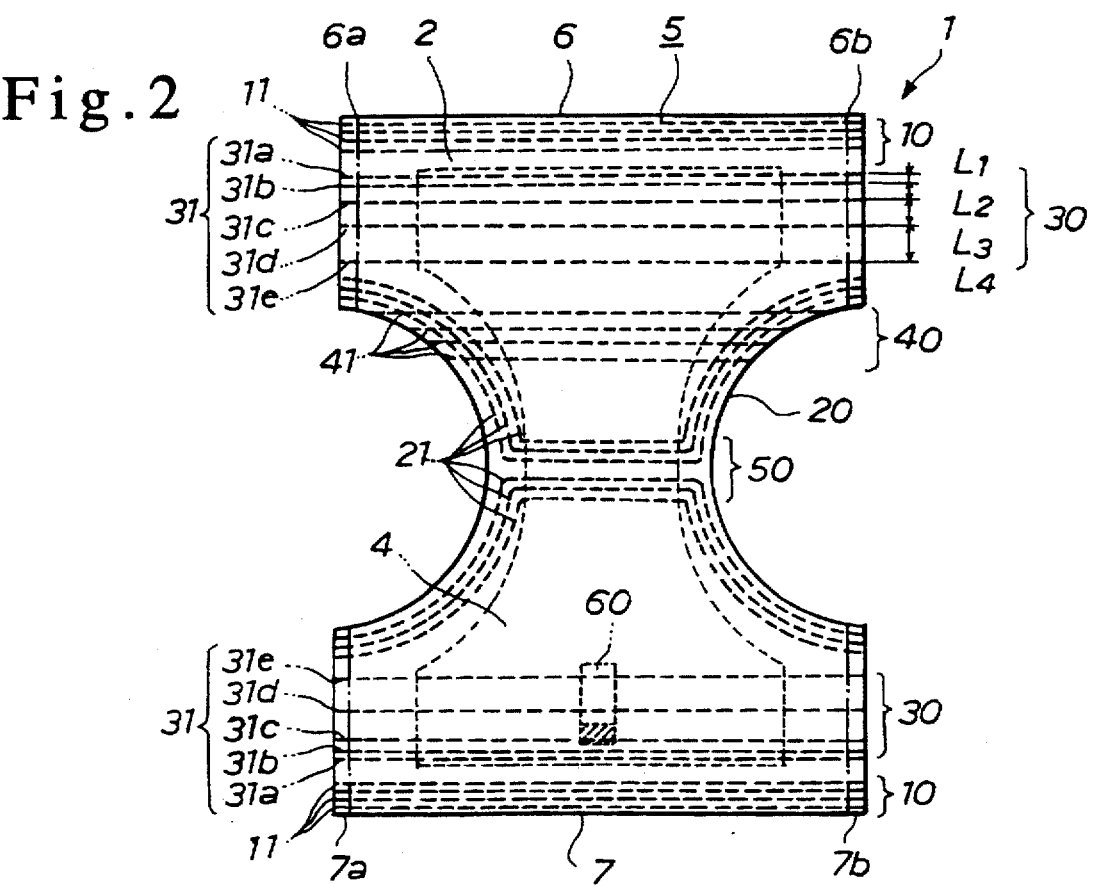
FIG. 2 is a plan view of the shorts type disposable diaper of FIG. 1 in an unfolded condition.

FIG. 1 is a perspective view of a preferred embodiment of the shorts type disposable diaper of the present invention, and FIG. 2 is a plan view of the shorts type disposable diaper shown in FIG. 1 in its unfolded condition.

The shorts type disposable diaper 1 of the embodiment shown in FIGS. 1 and 2 comprises an absorbent body 5 which comprises a liquid permeable topsheet 2, a liquid impermeable backsheet 3, and an absorbent member 4 interposed between the topsheet 2 and the backsheet 3. Opposing lateral side edges of a front waist body portion 6 corresponding to the front waist side of a wearer and those of a rear waist body portion 7 corresponding to the rear waist side of a wearer are joined and sealed together thereby forming a waist opening portion 10 and a pair of leg opening portions 20. Elastic members 11 and 21 are provided along the entire circumference of the waist opening portion 10 and the pair of leg opening portions 20, respectively, to form substantially continuous gathers. Further, a plurality of elastic members 31 are provided at a body-surrounding portion 30 which is located between the waist opening portion 10 and the pair of leg opening portions 20 and at which the absorbent member 4 is located, thereby forming substantially continuous gathers along the entire circumference of the body-surrounding portion 30.

Going into details, the lateral side edge 6a of the front waist body portion 6 and the lateral side edge 7a of the rear waist body portion 7 are joined and sealed together, and the lateral side edge 6b of the front waist body portion 6 and the lateral side edge 7b of the rear waist body portion 7 are joined and sealed together to form the joint portions 8 on each side.

The topsheet 2, the backsheet 3, and the absorbent member 4 each has an hourglass shape with its central portion narrowed. These members can be fabricated of the following materials.

The topsheet 2 is made of a liquid permeable sheet which transmits excretions to the absorbent member 4 and preferably feels like underwear. Such a liquid permeable sheet preferably includes woven fabric, nonwoven fabric, and porous film. Leakage of urine, etc. due to oozing from the periphery of the topsheet 2 can be prevented by a water-repellent treatment comprising coating the peripheral portion of the topsheet 2 with a hydrophobic compound such as silicone oil or paraffin wax, or coating the entire surface of topsheet 2 with a hydrophilic compound such as an alkyl phosphate followed by washing the peripheral portion with warm water.

A liquid impermeable and vapor permeable sheet obtained by stretching a filler-containing thermoplastic resin film is preferably used as the backsheet 3. Materials having a feeling close to underwear, such as a composite material composed of film and nonwoven fabric or a composite material of film and woven fabric, are used.

A combination comprising comminuted pulp as a main component and an absorbent polymer is preferably used as a material of the absorbent member 4. Additionally, a heat-treated mixture of a thermoplastic resin, cellulose fiber and an absorbent polymer is also preferred. The absorbent polymer may be present in any of the upper, middle and lower layers of the absorbent member and may be present as an admixture with pulp. The absorbent polymers preferably include those capable of absorbing and retaining 20 or more times its own weight of liquid and gelling on liquid absorption. Such absorbent polymers include a saponified starch-acrylic acid (or a salt thereof) graft copolymer, crosslinked sodium carboxymethyl cellulose, and an acrylic acid (or a salt thereof) polymer.

Four elastic members 11 are provided at the waist opening portion 10 of each of the front and rear waist body portions 6 and 7 at regular intervals. The elastic members 11 on the front waist body portion 6 and those on the rear waist body portion 7 are connected together by the aforesaid joining and sealing to form substantially continuous gathers along the entire circumference of waist opening portion 10.

Any of the elastic members conventionally employed in disposable diapers can be used as the elastic member 11 with no particular limitation. The elastic member 11 preferably has a band form. The elongation of the elastic member preferably ranges from about 80% to 140%. The term "elongation" as used herein has such a definition that when an elastic member having a length of e.g., 10 cm can be extended to 20 cm, that is, twice its own length, the elongation is 100%.

It is preferable that the elastic member 11 at the waist opening portion 10 has a stress at 30% elongation of about 50 to 150 g.

Three elastic members 21 are provided at the leg opening portion 20 of each of the front and rear waist body portions 6 and 7 at regular intervals. The elastic members 21 on the front waist body portion 6 and those on the rear waist body portion 7 each cross the absorbent member 4 at the crotch portion of the diaper and are connected together by the above-mentioned joining and sealing to form substantially continuous gathers along the entire circumference of the leg opening portion 20.

Any of the elastic members conventionally employed in disposable diapers can be used as the elastic member 21 with no particular limitation. The elastic member 21 preferably has a band form. The elongation of the elastic member 21 (elongation at the leg opening portion) preferably ranges from about 60% to 100%.

It is preferable that the elastic member 21 at the leg opening portion 20 has a stress at 30% elongation of about 40 to 100 gf.

The elastic members 21 cross the absorbent member 4 at the crotch portion 50 of the diaper in which the elongation of the elastic members is about 30 to 50%. The stress at 30% elongation of the elastic member at the crotch portion 50 is preferably about 40 to 100 g. If the stress were less than 40 gf, the absorbent member at the crotch portion would be contracted to have reduced absorbent capacity. If the stress exceeded 100 gf, the absorbent member would be deformed to have poor appearance.

Five elastic members 31 are provided at the body-surrounding portion 30 of each of the front and rear waist body portions 6 and 7, and those on the front waist body portion 6 and those on the rear waist body portion 7 are connected by the aforesaid joining and sealing to form substantially continuous gathers along the entire circumference of the body-surrounding portion 30.

The elastic member 31a which is closest to the waist opening portion 10 preferably has a stress at 30% elongation of from about 50 to 150 gf, still preferably from about 50 to 100 gf, while the elastic member 31e which is closest to the leg opening portion 20 preferably has a stress at 30% elongation of from about 40 to 100 g.

A fastening tape 60 to be used for the disposal of the diaper is provided on the outer surface of backsheet 3 of the rear waist body portion 7. A used diaper can be disposed hygienically by means of the fastening tape 60.

The joint portion 8 is formed by a known sealing technique, such as heat sealing, radiofrequency sealing, ultrasonic sealing, and the like.

The characteristic features of the first invention will be described below. As shown in FIGS. 1 and 2, the shorts type disposable diaper according to this preferred embodiment has a plurality of elastic members 41 provided at a urination point 40 located below the body-surrounding portion 30 and in the vicinity of the urination portion of the wearer, thereby forming continuous gathers in the width direction of the diaper. More specifically, four elastic members are provided on the front waist side at regular intervals.

The term "in the vicinity of the urination portion" as used herein means the portion corresponding to the urination portion of a wearer and the surrounding portions thereof. Specifically, it means the lower area of front waist body portion 6 which is located between the pair of leg opening portions 20.

Any of the elastic members conventionally employed in disposable diapers can be used as the elastic member 41 with no particular limitation. The elastic member 41 preferably has a string form and an elongation of about 50 to 80%.

While the number of the elastic members 41 adopted in this embodiment is 4, it is preferably 3 to 6. The stress at 30% elongation of the elastic member 41 is preferably about 40 to 100 gf, still preferably about 50 to 90 gf. If the stress were less than 40 gf, the front waist body portion unavoidably would have a partially swollen shape. If the stress exceeded 100 g, the absorbent member would be deformed to have poor appearance.

The interval of the elastic members 41 is not particularly limited and may be selected arbitrarily as far as the advantageous effects of the present invention are not impaired.

Since the shorts type disposable diaper of this embodiment has elastic members in the urination point 40, it has an improved fit at the urination point 40 and thereby as a whole. Even with the weight of the waste materials, the diaper does not get out of the position while it is worn and thereby effectively prevent leakage.

A hip length to width ratio of the above-described disposable diaper is preferably about 1.10 to 1.30, still preferably about 1.15 to 1.30. If the ratio were less than 1.10, the hip length would be too short to cover the navel of the diaper wearer, easily causing leakage from the waist opening portion. If the ratio exceeded 1.30, the shorts type diaper would have a loose fit and tends to slide down.

The term "hip length" as used herein is intended to denote the length from the bottom edge to the upper edge of the waist opening portion 10 with all the elastic members extended to their full length. The term "hip width" as used herein is intended to denote the length between the opposing lateral side edges with all the elastic members extended to their full length.

The characteristic features of the second invention will be described below. The elastic members 31 provided at the body-surrounding portion 30 are disposed in such a manner that the interval of the elastic members 31 becomes narrower towards the waist opening portion 10 and that the elastic members 31 provided at the body-surrounding portion have an increasing elongation towards the waist opening portion 10.

Any of the elastic members conventionally employed in disposable diapers can be used as the elastic member 31 with no particular limitation. The elastic member 31 preferably has a string form and an elongation of about 80 to 120%.

The elastic members 31 are preferably disposed at such an interval that the $L_1:L_2:L_3:L_4$ (see FIG. 2) ratio is 1:1.0 to 1.5:1.5 to 2.0:2.0 to 2.5.

The elongation of the elastic members 31 preferably increases in the upward direction (from the crotch portion to the waist opening portion 10) by about 5 to 15%. The total change of increase in elongation is preferably about 40%.

Since the shorts type disposable diaper according to this embodiment has the elastic members provided at the body-surrounding portion and disposed in such a manner that the intervals getting narrower and the elongation increases as they approach the waist opening portion 10, the whole diaper exhibits a good fit and does not slide down while it is worn even with the weight of the waste materials imposed. As a result, it effectively prevents leakage of the waste materials without applying excessive pressure to the wearer's body, that is, without impairing wearer's comfort.

The shorts type disposable diaper according to the present invention is by no means limited to the aforesaid particular embodiments. For example, included in the present invention is an embodiment in which the elastic members at the waist opening portion 10 and elastic members at the urination point 40 have the same feature as those at the body-surrounding portion, i.e., the interval getting narrower and the elongation increasing as they approach the waist opening portion 10.

Industrial Applicability

The shorts type disposable diaper according to the present invention (the first invention) has elastic members at the urination point to form gathers in the width direction of the diaper, by which the diaper has an improved fit at the urination point. Therefore, even after a wearer discharges the waste materials, the diaper does not get out of the position, does not partly swell out, does not deteriorate the appearance, and, as a result, does not cause leakage of the waste materials.

The shorts type disposable diaper according to the present invention (the second invention) has elastic members disposed at the body-surrounding portion in such a manner that the interval gets narrower and the elongation increases towards the waist opening portion. Therefore, dense gathers are provided in portions which are subject to stretching and contraction to the accompaniment of a wearer's movement, while loose gathers are provided in portions which are not so deformed. Accordingly, the diaper has an improved fit without impairing wearer's comfort, and even after a wearer discharges the waste materials the diaper does not get out of the position and, as a result, causes no leakage of body wastes.

Hence, the shorts type disposable diaper according to the present invention (inclusive of the first and second inventions) exhibits an excellent fit without impairing wearer's comfort, does not get out of the position due to the weight of the waste materials, and causes no leakage.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A shorts type disposable diaper comprising an absorbent body which comprises a liquid permeable topsheet, a liquid impermeable backsheet, and an absorbent member interposed between the topsheet and the backsheet, the absorbent body having a front waist body portion located on the stomach side of a diaper wearer when the diaper is worn and a rear waste body portion located on the back side of the wearer, the front and rear waist body portions being joined and sealed together at opposing lateral side edges thereof to form a waist opening portion and a pair of leg opening portions, each of the waist opening portion and the pair of leg opening portions being provided with an elastic member which forms substantially continuous gathers along the entire circumstance of the waist opening portion and the leg opening portions, and a plurality of elastic members being provided at a body-surrounding portion which is located between the waist opening portion and the pair of leg opening portions and at which the absorbent member is provided, forming substantially continuous gathers along the entire circumference of the body-surrounding portion, said elastic members provided at the body-surrounding portion are disposed in such a manner that the placement of the elastic members relative to each other becomes narrower towards the waist opening portion and that the elastic members provided at the body-surrounding portion have an increasing elongation towards the waist opening portion, the diaper having a plurality of elastic members provided at a urination point located below the body-surrounding portion and adjacent the urination portion of the wearer, said urination point being a lower area of said front waist body portion located between said leg opening portions, thereby forming continuous gathers in the width direction of the diaper, whereby said elastic members stably support said diaper on said wearer to prevent leakage of waste materials.

2. The shorts type disposable diaper according to claim 1, wherein a hip length to width ratio of the diaper is about 1.10 to 1.30, said hip length is a length from one of said leg opening portions to said waist opening portion, said hip width is a length between said opposing lateral side edges.

3. The shorts type disposable diaper according to claim 1, wherein the elastic member provided at the body-surrounding portion and closest to the waist opening portion has a stress at 30% elongation of generally 50 to 150 gf, and the elastic member provided at the body-surrounding portion and closest to the leg opening portions has a stress at 30% elongation of from about 40 to 100 gf.

4. The shorts type disposable diaper according to claim 1, wherein the elastic member provided at the urination point has a stress at 30% elongation of generally about 40 to 100 gf.

5. The shorts type disposable diaper according to claim 1, wherein an elastic member is provided at the crotch portion along the width direction of the diaper, and the elastic member has a stress at 30% elongation of generally about 40 to 100 gf.

6. The shorts type disposable diaper according to claim 1, wherein a fastening tape to be used for disposal of the diaper is provided on the outer surface of the backsheet of the rear waist body portion.

7. A shorts type disposable diaper comprising an absorbent body which comprises a liquid permeable top sheet, a liquid impermeable backsheet, and an absorbent member interposed between the topsheet and the backsheet, the absorbent body having a front waist body portion located on the stomach side of a diaper wearer when the diaper is worn and a rear waist body portion located on the back side of the wearer, the front and rear waist body portions being joined and sealed together at opposing lateral side edges thereof to form a waist opening portion and a pair of leg opening portions, each of the waist opening portion and the pair of leg opening portions being provided with an elastic member which forms substantially continuous gathers along the entire circumference of the waist opening portion and the leg opening portions, and a plurality of elastic members being provided at a body-surrounding portion which is located between the waist opening portion and the pair of leg opening portions and at which the absorbent member is provided, forming substantially continuously gathers along the entire circumference of the body-surrounding portion, the diaper having the elastic members provided at the body-surrounding portion disposed in such a manner that the placement of the elastic members relative to each other becomes narrower towards the waist opening portion and that the elastic members provided at the body-surrounding portion have an increasing elongation towards the waist opening portion, each elastic member being subjected to generally a same stress, whereby said elastic members stably support said diaper on said wearer to prevent leakage of waste materials.

8. The shorts type disposable diaper according to claim 7, wherein the elongation of each of the respective elastic members provided at the body-surrounding portion increases in the upward direction from the crotch portion to the waist opening portion from generally 5 to 15%.

* * * * *